(12) United States Patent
Fleener et al.

(10) Patent No.: US 6,908,427 B2
(45) Date of Patent: Jun. 21, 2005

(54) FLEXIBLE ENDOSCOPE CAPSULE

(75) Inventors: Richard P. Fleener, Englewood, CO (US); Robert L. Bromley, Littleton, CO (US)

(73) Assignee: Paré Surgical, Inc., Englewood, CO (US)

(*) Notice: Subject to any disclaimer, the term of this patent is extended or adjusted under 35 U.S.C. 154(b) by 159 days.

(21) Appl. No.: 10/334,495

(22) Filed: Dec. 30, 2002

(65) Prior Publication Data

US 2004/0127767 A1 Jul. 1, 2004

(51) Int. Cl.$^7$ .................................................. A61B 1/00
(52) U.S. Cl. ........................ 600/104; 600/106; 600/127
(58) Field of Search .................................. 600/104, 106, 600/121, 123, 127, 129

(56) References Cited

U.S. PATENT DOCUMENTS

| | | | |
|---|---|---|---|
| 5,588,951 A | 12/1996 | Zhu et al. | 600/207 |
| 5,662,585 A | 9/1997 | Willis et al. | 600/104 |
| 5,762,604 A | 6/1998 | Kieturakis | 600/115 |
| 5,976,073 A * | 11/1999 | Ouchi | 600/129 |
| 6,206,823 B1 | 3/2001 | Kolata et al. | 600/129 |
| 6,524,234 B2 * | 2/2003 | Ouchi | 600/127 |
| 6,689,051 B2 * | 2/2004 | Nakada et al. | 600/140 |
| 6,689,130 B2 * | 2/2004 | Arai et al. | 606/46 |
| 6,699,180 B2 * | 3/2004 | Kobayashi | 600/127 |

OTHER PUBLICATIONS

Quik–Stitch Endoscopic Suturing System, 2002 Edition, by Paré Surgical, Inc. (2 Pages).
Quik–Stitch Endoscopic Sutrung System, by Paré Surgical, Inc. (2 Pages).

* cited by examiner

Primary Examiner—Beverly M. Flanagan
(74) Attorney, Agent, or Firm—Marsh Fischmannn & Breyfogle LLP

(57) ABSTRACT

An endoscopic capsule adapted for selective attachment to the distal end portion of an endoscopic device. The capsule is designed for insertion with an interconnected endoscopic device into a patient body to provide an open space in front of the distal end of the endoscopic device. The capsule facilitates the performance of endoscopic procedures providing a space in which to manipulate medical instruments within the patient body as well as improving a surgeon's field of vision within the patient body. In one embodiment, the capsule includes a housing having an internal chamber and two apertures. A first aperture is interconnectable to the end of an endoscopic device and provides operative access to endoscopic instruments contained therein. One or more of these endoscopic devices are advanceable into the internal cavity for selectively engaging patient tissue disposed relative to the second aperture.

47 Claims, 6 Drawing Sheets

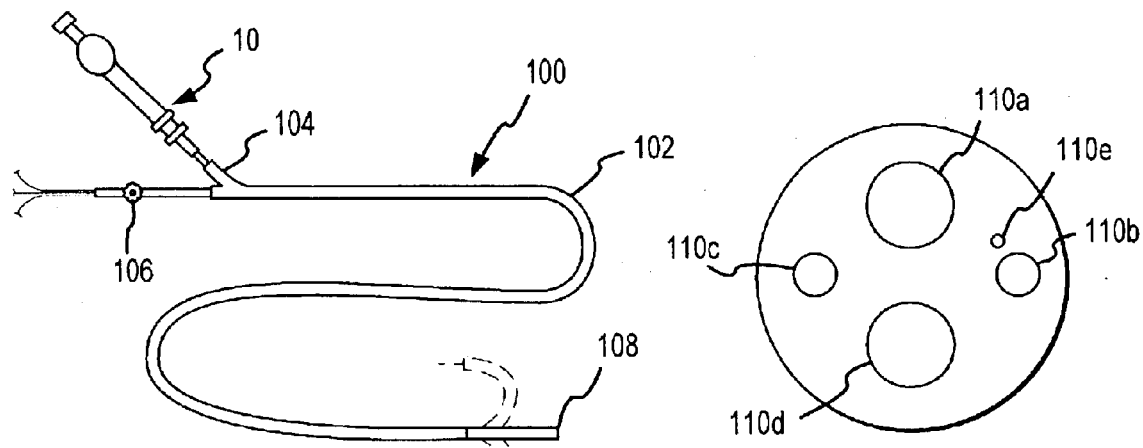
FIG.5a
FIG.5b
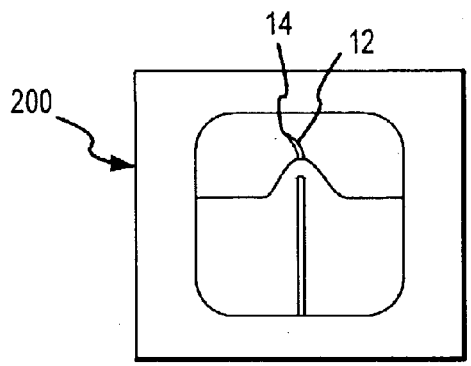
FIG.5c

FLEXIBLE ENDOSCOPE CAPSULE

FIELD OF THE INVENTION

The present invention relates to the field of minimally invasive internal surgery, and more particularly, to facilitating endoscopic procedures.

BACKGROUND OF THE INVENTION

Minimally invasive internal surgery procedures are ever-increasing. Such procedures typically entail the insertion of one or a plurality of tubular members into a patient body and the passage of various devices through the tubular member(s) to access a tissue site of interest.

In certain endoscopic procedures, a tubular member is inserted through a bodily orifice to provide instrumentation access therethrough to an internal tissue site, e.g., through the mouth or anus to access the "lumen" or cavity of a hollow organ. The tubular member generally contains a plurality of individual channels extending along its entire length for providing, inter alia, suction, water, and/or air as well as providing access for optical equipment and medical instruments. Given such access points and associated bodily canals, the tubular members utilized in endoscopic applications are necessarily of flexible construction and may be of significant length. To date, endoscopic procedures have been largely limited to gasdroesophergeal (GERD) and biopsy applications. However, it is believed that new surgical devices and procedures may be developed that facilitate increased endoscopic applications involving, inter alia, the ligating, proximating and suturing of tissue in the stomach and colon.

Common to many proposed endoscopic surgical devices and procedures is the need to manipulate a medical instrument relative to an internal tissue site of interest. As may be appreciated, the completion of medical procedures in endoscopic applications can present a challenging and sometimes tedious task for surgical personnel. For example, suturing procedures may involve difficult manipulation of an external device to cause an internally located needle to pass entirely through tissue at a surgical site to effect suture stitching. An additional problem that may be encountered during these endoscopic medical procedures is that while the endoscope is inserted within the hollow cavity of an organ, these organs are generally in a flaccid or relaxed state. That is, internal tissue, such as esophageal and intestinal tissue, is often flaccid and in direct contact with the insertion end of the endoscopic device. In this regard, a physician may have a limited field of view of a tissue site area of interest as well as little room in which to manipulate medical instruments relative to the tissue site to perform a desired medical procedure. In addition, relaxed tissue does not provide a structural surface against which the endoscope may apply pressure during a procedure.

SUMMARY OF THE INVENTION

An objective of the present invention is to provide an apparatus and method that facilitates the performance of endoscopic medical procedures.

Another objective is to provide an apparatus and method for facilitating the performance of endoscopic medical procedures in a minimally complex manner.

A further objective is to provide an apparatus and method that facilitates performing endoscopic medical procedures via an approach that is compatible with existing endoscopic devices.

One or more of the above-noted objectives and additional advantages are realized by the present invention that comprises an endoscopic capsule adapted for selective attachment to the distal end portion of an endoscopic device. The capsule is designed for insertion with an interconnected endoscopic device into a patient body to provide an open space in front of the distal end of the endoscopic device thereby improving a surgeon's field of vision as well as providing a space in which to manipulate medical instruments within the patient body.

In one aspect of the invention, the capsule includes a housing defining an internal chamber for selective attachment to the distal end of an endoscopic device (e.g., a single or multi-lumen tubular member). A first aperture extends through the housing to the internal chamber to provide operative access for a medical device associated with the endoscopic device. In one embodiment, the first aperture is sized to provide access to the internal chamber to a medical device that is advanceable relative to the distal end of the endoscopic device. Further, a second aperture extends through the housing to the internal chamber to provide access for a medical device to patient tissue disposed adjacent to the second aperture during an endoscopic procedure. That is, the housing is selectively attachable to the end of an endoscopic device and a medical device associated with that endoscopic device may access the internal chamber of the housing through the first aperture and then access patient tissue disposed adjacent to the second aperture. As will be appreciated, the internal chamber defined by the housing provides an open space relative to the second aperture that may be utilized to manipulate a medical device relative to the tissue and/or manipulate the tissue. By way of example, the capsule may be interconnected to the distal end of a multi-lumen endoscopic device utilized for esophageal and/or colorectal procedures. As will be appreciated, such multi-lumen endoscopic devices may provide internal patient access to a plurality of medical devices, including without limitation, remote imaging devices, illumination devices, as well as medical instruments such as scalpels and suturing devices. These medical devices may be externally manipulated to perform a desired medical procedure, which may include, inter alia, advancing one or more of these devices beyond the distal end of the endoscopic device and into the internal chamber of the housing member from where the patient tissue may be engaged through the second aperture. However, it will be further appreciated that the endoscopic capsule may also be utilized with single lumen endoscopic devices and/or a plurality of endoscopic devices to perform, e.g., laparoscopic procedures.

Additions and variations of the noted features exist. These refinements and additional features may be provided separately or in any combination. For instance, the first and second apertures may be oriented relative to one another in any manner that allows access for one or more medical devices to the internal chamber, as well as access for one or more medical devices to patient tissue adjacent to the second aperture. For example, the center axes for the first and second apertures may be transverse to one another. In this regard, the first aperture may extend through a distal end of the housing and the second end of the aperture may extend through a sidewall of the housing. Furthermore, the housing may contain additional apertures to provide access to other tissue areas adjacent to the housing member, or, contain perforations to allow fluids to pass through the housing.

As noted, the first aperture extends through the housing to the internal chamber and provides operative access for a medical device associated with the endoscopic device to the internal chamber. In this regard, the first aperture will generally interconnect the housing to the distal end of the endoscopic device and may be sized to matingly receive the distal end of the endoscopic device. In another embodiment, the first aperture is sized to slidably receive the distal end of the endoscopic device thereby allowing a portion of the housing to slide over a portion of the endoscopic device. In a further embodiment where the first aperture slidably receives the distal end of the endoscopic device, the first aperture is adaptable to receive the distal end of differently sized endoscopic devices, allowing the present invention to be utilized with a variety existing endoscopic devices. That is, the aperture may expand or contract to mate with endoscopic devices of varying sizes.

The housing member may have any geometric shape that provides an internal chamber sized for allowing selective manipulation of a medical device relative to patient tissue disposed adjacent to the second aperture. However, it will be appreciated that due to the constraints of the environment in which the capsule is utilized, that the capsule will generally be tubular to match the end of the endoscopic device and/or elongated to provide an internal chamber having a volume that permits selective manipulation of one or more medical devices therein. In this regard, the housing will generally have a diameter between about 4 mm and about 28 mm. Furthermore, when the housing is an elongated member, it will have a length between about 15 mm and about 76 mm.

In any housing configuration, the second aperture has to be large enough to allow access to patient tissue disposed adjacent to the capsule. That is, the second aperture must provide a port large enough to locate tissue areas of interest and/or perform medical procedures on these tissue areas of interest. In this regard, the second aperture will generally have a length between about 4 mm and about 37 mm and an angular width between about 45° and about 270°. As will be appreciated, the overall size of the second aperture is generally a function of the size of the endoscopic device with which it is utilized. For example, capsules utilized for arterial applications will necessarily be smaller than end caps utilized for esophageal applications with the corresponding reduction in size of the second aperture.

The housing may be formed of any material that provides the necessary structural rigidity to allow the capsule to be inserted within a patient lumen without collapsing. Generally, the capsule will comprise a semi-rigid material that maintains the internal chamber during endoscopic procedures. Further, the housing may be formed of a polymeric material that allows the capsule to be easily manufactured (e.g. injection molded). In another embodiment, the housing comprises a substantially transparent material that allows an imaging device to view the tissue disposed adjacent to the outside surface of the housing.

According to a second aspect of the present invention, an endoscopic device is provided that includes a tube member having a distal end adapted for insertion into a patient body, an endoscopic instrument positionable through the tube member, and a housing having an internal chamber interconnected to the distal end of the tube member. This housing has first and second apertures extending through a sidewall to provide operative access for one or more of the endoscopic instruments to the internal chamber. That is, a first aperture allows one or more endoscopic instruments, which are positionable through the tube member, to have operative access to the internal chamber. For example, light sources and/or imaging devices may illuminate and image the internal chamber. Furthermore, endoscopic instruments may be advanced beyond the distal end of the tube member through the first aperture and into the internal chamber. That is, one or more endoscopic instruments may extend through the tube member and into the internal chamber of the housing.

The endoscopic instruments are generally selected from a group consisting of imaging devices, light sources, and medical instruments. Additionally, as many tube members contain a plurality of lumens, two or more endoscopic instruments may be positioned through the tube member thereby allowing a plurality of instruments to simultaneously access the internal chamber of the housing member. Furthermore, it will be noted that many endoscopic devices utilize one or more lumens for irrigation and/or suction. Accordingly, irrigants and vacuum may also be applied to/through the housing member.

Imaging devices include any flexible apparatus that may be disposed through the tube member, including, without limitation, fiber optic devices and camera devices. As will be appreciated, any imaging device will also typically include a remote display device operable to provide real time images from the imaging device. In addition to having operative access (e.g., line of sight) to the internal chamber of the housing member, these imaging devices may themselves be advanceable into the internal chamber of the housing member to allow selective imaging of patient tissue through, for example, the second aperture and/or a transparent sidewall of the housing.

The medical instruments that are disposable through the tube member may include any endoscopic compatible instrument for performing a medical procedure to patient tissue. These devices include, without limitation, scalpels, cauterizing units, snares, and/or suturing devices. As may be appreciated, any of the above-noted medical instruments may include one or more sub-components. For example, the suturing device may comprise a needle, suturing material, and/or some sort of grasping member to selectively attach the suturing material to the needle.

Once an endoscopic instrument has been advanced into the internal chamber, that instrument may be utilized to engage patient tissue disposed relative to the second aperture. For example, one or more endoscopic instruments may be selectively advanceable and/or retractable through the second aperture to engage patient tissue disposed outside of the housing. Alternatively, patient tissue may be disposed through the second aperture allowing for tissue engagement/manipulation within the internal chamber of the housing. For example, a lumen in the tube member may be a vacuum port operable to pull a portion of the patient tissue through the second aperture into the internal chamber, wherein it may be selectively engaged by one or more endoscopic instruments.

According to another aspect of the present invention, a method for performing an endoscopic procedure is provided. The method includes the steps of positioning an endoscopic capsule within a patient body adjacent to a target area of patient tissue. This capsule has an internal chamber and is disposed on the end of an endoscopic device for placement relative to the target area of patient tissue. An aperture on the capsule is then positioned (e.g., aligned) with the target area of tissue to provide access from the internal chamber to the target area of tissue. Once so positioned, a medical device associated with the endoscopic device to which the capsule is attached, or, from a separate endoscopic device may be advanced into the internal chamber of the capsule and be utilized to perform a medical procedure on the target area of patient tissue disposed adjacent to the aperture.

Positioning the capsule relative to the target area of tissue provides a working space (e.g., the internal chamber) adjacent to the target area of tissue. In the case of esophageal and colorectal procedures, positioning may also have the effect of dilating a collapsed patient lumen. As will be appreciated, the step of positioning generally entails the external manipulation (e.g., advancement, retraction, and/or rotation) of the endoscopic device to which the capsule is attached. Illumination and imaging devices associated with the endoscopic device and/or other endoscopic devices may be utilized during positioning of the capsule as well as performance of medical procedures. Once positioned the internal chamber of the capsule provides an open space in which an endoscopic medical device may be disposed for performing medical procedures on the target area of patient tissue. This medical device may be disposed through the aperture adjacent to the target area of patient tissue, or, through a second aperture extending through the capsule.

The medical instrument disposed within the internal chamber of the capsule may be utilized to perform passive medical procedures (e.g., diagnostic imaging), or, to perform active medical procedures wherein the patient tissue is engaged (e.g., cut, sutured, cauterized etc.). In either case, a portion of a medical instrument may be disposed through the aperture relative to the target area of patient tissue, or, a portion of the target area of patient tissue may be disposed through the aperture into the internal chamber for manipulation therein. In this regard, the step of disposing tissue within the internal chamber may include the steps of physically contacting the tissue and pulling that tissue through the aperture; pressing the capsule into contact with the tissue; and/or applying suction through the capsule to draw tissue therein.

The method necessarily includes the step of interconnecting the capsule to the distal end of an endoscopic device to allow placement within a patient body. When utilizing capsules designed for use with existing endoscopic devices (e.g., disposable capsules), interconnection may be performed at a medical care facility. However, it will be appreciated that interconnection of the capsules to the distal end of an endoscopic device may be done by a manufacturer of the endoscopic device.

According to another aspect of the present invention, a method for performing an endoscopic procedure is provided. The method includes the steps of positioning an endoscopic capsule relative to a target area of patient tissue within a patient body, wherein the endoscopic capsule has an internal chamber and at least one aperture extending through the capsule to the internal chamber. Accordingly, the aperture(s) extending through the capsule may be positioned adjacent to the target area of tissue to facilitate the performance of endoscopic procedures thereon. The method further includes disposing a portion of the target area tissue through the aperture and at least partially restricting movement of this tissue relative to the aperture in conjunction with inserting a needle through the tissue.

The step of disposing tissue through the aperture may be performed in any applicable manner. For example, the tissue may be physically manipulated through the aperture utilizing an endoscopic instrument. In one embodiment, the needle that is inserted through the target area tissue in conjunction with restricting step may be utilized to physically manipulate the tissue through the aperture. In this regard, a distal end of the needle may be advanced through the aperture to engage a portion of the tissue whereupon the needle may be lifted and/or rotated to pull the tissue through the aperture and thereby complete the disposing step. Alternatively, suction may be utilized to pull a portion of the tissue through the aperture. In this regard, a second aperture associated with the capsule may be operatively interconnected to a suction lumen of an endoscopic device. Additionally, if the patient tissue is sufficiently flaccid, a portion of the tissue may be disposed through the aperture through physical manipulation of the endoscopic capsule (e.g., the capsule may be pressed into direct contact with the tissue). Accordingly, this may require external manipulation of the endoscopic device to which the endoscopic capsule is interconnected.

The step of restricting generally entails restricting the movement of tissue in at least in the first direction relative to the aperture. In this regard, the tissue may be contacted (e.g., pressed) against a rim portion of the aperture to restrict its movement. As noted, the step of inserting the needle through the tissue is performed in conjunction with restricting the movement of the tissue. In one embodiment, the needle is utilized to press a portion of the tissue disposed through the aperture against an opposing rim surface of the aperture. Prior to the needle piercing the tissue, the tissue is compressed between the distal end needle and the rim surface of the aperture. As will be appreciated, continued advancement of the needle results in the needle piercing the tissue.

In a further embodiment of the present aspect, suture material is passed through the tissue along with the needle to perform endoscopic suturing of the target area of tissue. In this regard, the suture material may be held adjacent to the distal end of the needle utilizing, for example, a grasping member associated with the needle. Accordingly the suture material is drawn through the tissue as the needle passes through the tissue. Once disposed through the tissue, the suture material may be released relative to the needle and the needle may be withdrawn. At this point, an end of the suture material is disposed through the target area of tissue where it may be reengaged by the needle and disposed through additional tissue sites and/or tied to form a suture.

Additional aspects and advantages of the present invention will become apparent to those skilled in the art upon consideration of the further description provided hereinbelow.

BRIEF DESCRIPTION OF THE DRAWINGS

FIG. 5a illustrates an endoscopic system with which the present invention may be utilized.

FIG. 5b is an end view of the distal end of the endoscopic device illustrated in FIG. 5a.

FIG. 5c illustrates a display device employable in the system of FIG. 5a.

DETAILED DESCRIPTION

Figure 1:
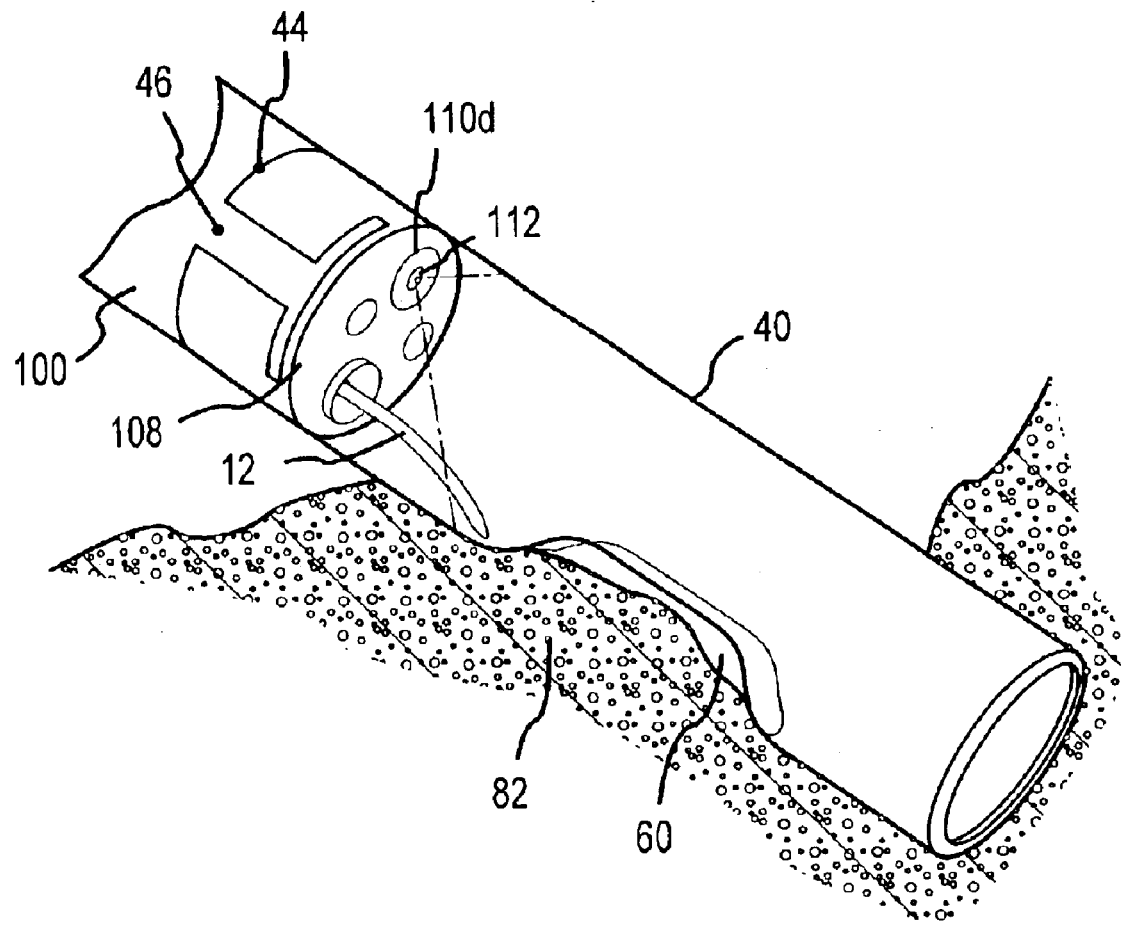
FIG. 1 shows a perspective view of a first embodiment of the present invention.
Figure 2:
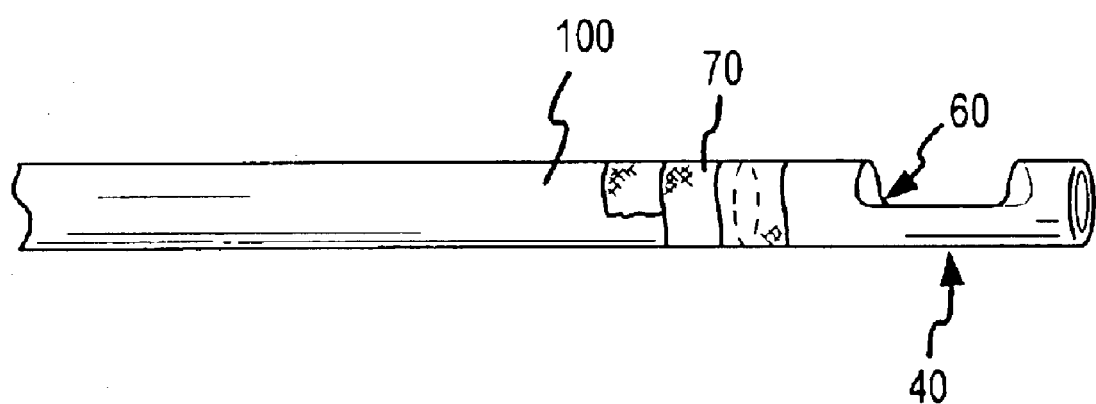
FIG. 2 shows the first embodiment of the present invention affixed to the distal end of an endoscopic device.

FIGS. 1 and 2 illustrate a first embodiment of an end cap 40 that may be interconnected to an endoscopic device 100.

The end cap 40 provides an improved field of view for endoscopic imaging device 112 as well as working space for endoscopic medical instruments to perform medical procedures. As used herein, the term endoscopic device includes a plurality of minimally invasive surgical devices (i.e., scopes) that have been developed for specific uses. For example, upper and lower endoscopes are utilized for accessing the esophagus/stomach and the colon, respectively, angioscopes are utilized for examining blood vessels, and laparoscopes are utilized for examining the peritoneal cavity. Though discussed herein in relation to use with endoscopic devices such as the type utilized for colon and esophageal applications, it will be appreciated that numerous other embodiments including one or more aspects of the present invention may be constructed for use with any minimally invasive surgical device.

The end cap 40 is a substantially hollow member that provides an open or working space in front of the insertion or distal end 108 of an endoscopic device 100. This working space may be utilized to manipulate one or more endoscopic instruments 12 relative to a tissue site 80 of interest during an endoscopic procedure. As shown in FIG. 1, the end cap 40 may be utilized in instances where flaccid tissue would otherwise collapse around the end of an endoscopic device. The end cap 40 is formed of a substantially clear material, allowing a surgeon to view patient tissue 80 disposed on the outside surface of the end cap 40. Furthermore, the end cap 40 is formed from semi rigid plastic material that prevents the end cap 40 from collapsing during use. That is, the end cap 40 maintains an open internal chamber 50 during endoscopic procedures.

Referring to FIG. 1, the dashed lines represent the field of view provided to an optical device 112 inserted through a first port 110d the distal end 108 of the endoscopic device 100. It will be appreciated that the optical device 112 may move in relation to the end cap 40 providing improved imaging for all areas inside the end cap 40. In any case, the working space provides a surgeon with an increased field of view during endoscopic procedures as represented by the dashed lines in FIG. 1. Though shown as having a relatively narrow field of view for illustrative purposes, it will be noted that a field of view on nearly 180° may be achieved. As will be appreciated, most endoscopic devices 100 utilize a single optical device 112 creating a monocular view, which can make performing medical procedures difficult due to the lack of depth perception. In this regard, the end cap 40 can also provide a visual gauge to facilitate medical procedures. For example, the end cap 40 contains a tissue access port 60 (as will be more fully discussed herein) along a portion of its length. Accordingly, a surgeon can utilize the position of a medical instrument 12 relative to an edge of the tissue access port 60 as a visual gauge.

The end cap 40 is a generally hollow cylindrical element that fits over the distal end 108 of an endoscopic device 100. In this regard, the end cap 40 contains an outside diameter similar to the outside diameter to the distal end 108 of the endoscopic device 100. While generally circular, the size of the distal end of endoscopic devices may vary depending on their intended use. To accommodate endoscopic devices of varying sizes, the attachment end 44 of the end cap 40 contains an aperture split 46. This aperture split 46 allows the attachment end 44 to expand to fit over larger endoscopic devices, or, to contract to fit smaller endoscopic devices. For most esophageal/colon applications, an end cap 40 having a diameter of about seven-sixteenths of an inch has been found to accommodate most endoscopic devices. However, end caps 40 having other diameters may also be manufactured.

The end cap 40 may be secured to the distal end 108 of the endoscopic device using any appropriate means. As shown in FIG. 2, the end capsule 40 is secured to the endoscopic device 100 utilizing surgical tape 70, which has been found to provide adequate retention in a cost efficient manner while allowing simplified production of the end cap 40. However, it will be appreciated that other attachment mechanisms may be incorporated, such as, but not limited to, threaded connectors and/or snap-fit means.

Figure 3A:
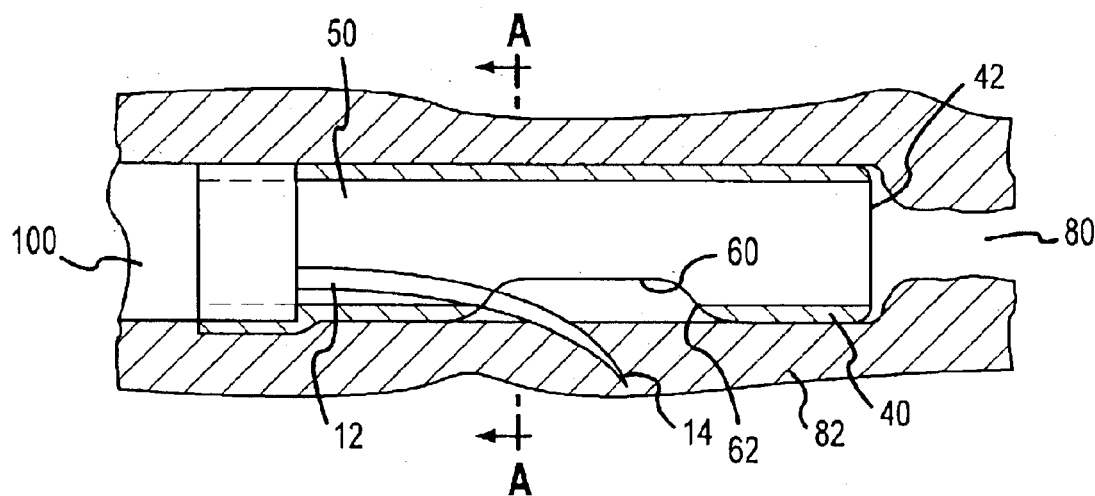
FIGS. 3a–3c show the cross-sectional views and an end view of the first embodiment of the present invention inserted within a tissue lumen.
Figure 3B:
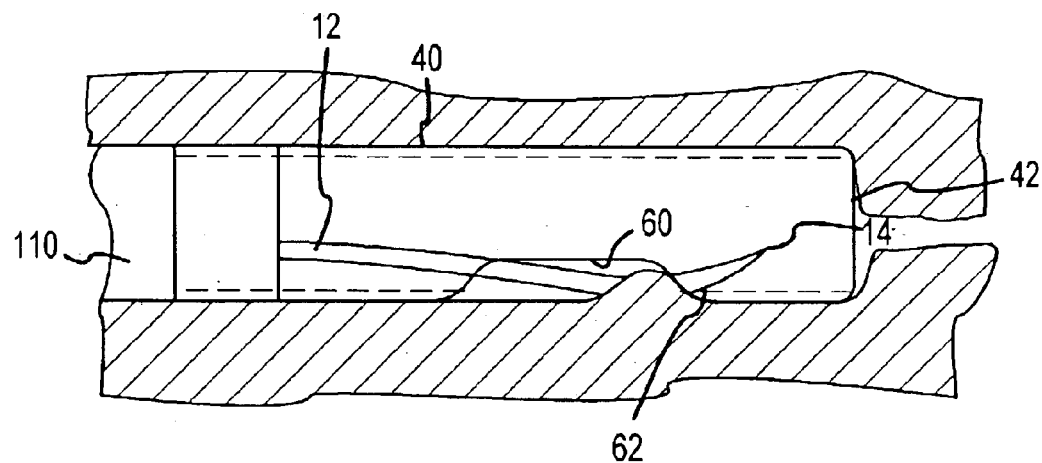
Figure 4A:
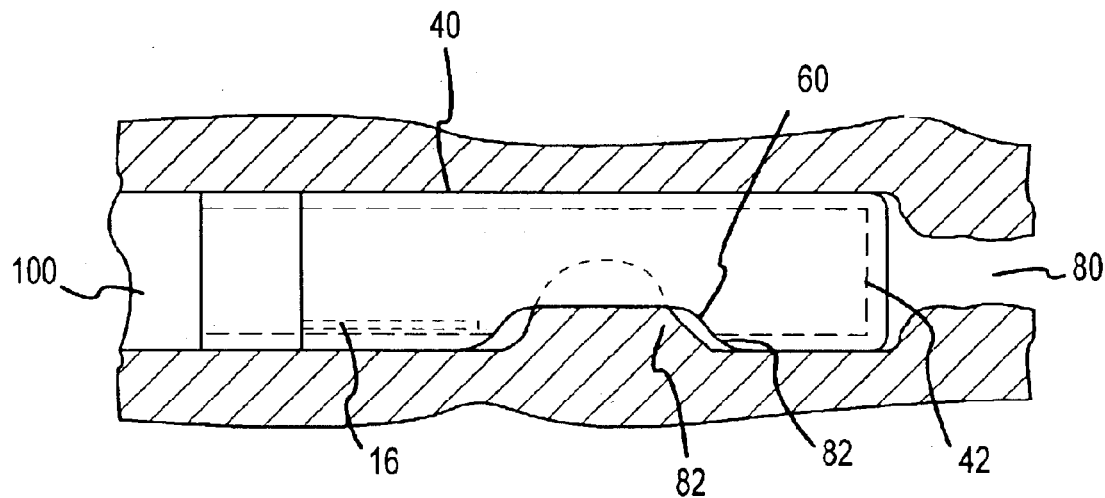
FIGS. 4a and 4b show two cross-sectional views of a second embodiment of the present invention inserted within a tissue lumen.
Figure 4B:
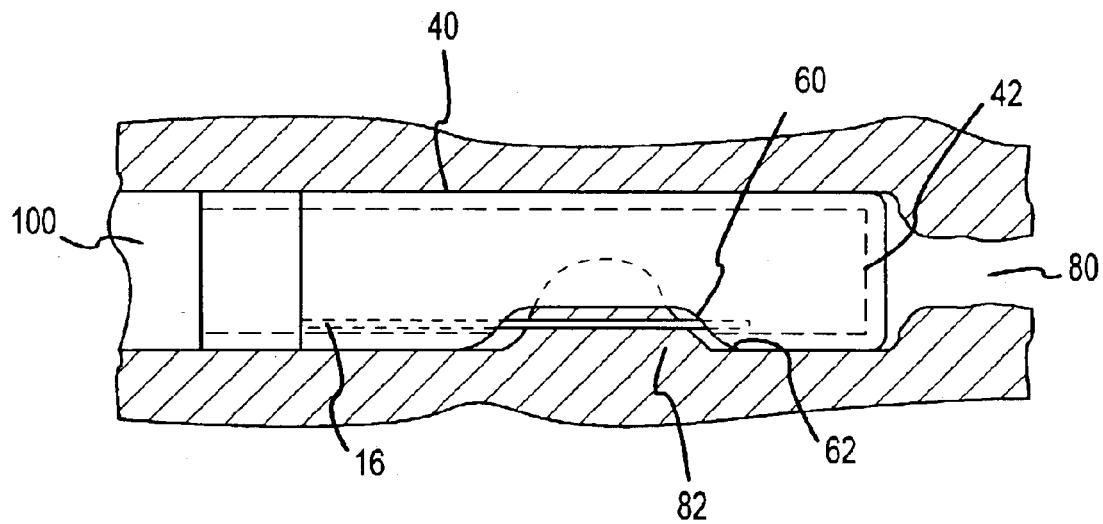

As noted, the attachment end 44 of the substantially hollow cylindrical end cap 40 is open defining an aperture to receive the distal end 108 of an endoscopic device 100. In this regard, the end cap 40 defines an internal chamber 50 that is accessible by endoscopic instruments through the distal end 108 of the endoscopic device 100. Referring to FIG. 3a, a cross-sectional view of the end cap 40 interconnected to the distal end of the endoscopic device 100 is shown. As illustrated, the attachment end 44 of the end cap 40 receives the distal end of the endoscopic device 100. Accordingly, medical instruments, such as a needle 12, can access the internal chamber 50 of the end cap 40. In the embodiment of FIGS. 3a and 3b, the distal end 42 of the end cap 40 is open. This allows suction or irrigation provided by the endoscopic device 100 to pass through the end cap 40 unimpeded. FIGS. 4a and 4b show a second embodiment of the end cap 40 where the distal end 42 of the end cap 40 is closed to allow suction from the endoscopic device 100 to pull tissue into the access port 60, as will be discussed herein.

As shown in FIG. 3a, the end cap 40 and endoscopic device 100 are inserted through a patient lumen 80. As shown, the walls 82 of the lumen 80 are initially collapsed. As the end cap 40 advances, the lumen 80 dilates to allow the end cap 40 and endoscopic device 100 to pass through. That is, the hollow end cap 40 passively retracts the walls 82 of the patient lumen 80, providing a working space for the endoscopic instruments while additionally providing a field of view for the endoscopic device 100.

Figure 3C:
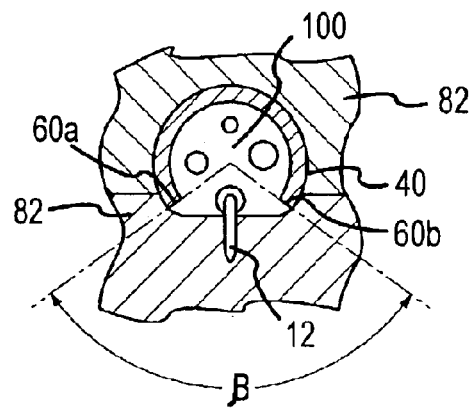

The end cap 40 also includes a patient tissue access port 60 that allows a medical device associated with the endoscopic device 100 to access patient tissue disposed relative to the outside surface of the end cap 40. The cross-sectional and end views of FIGS. 3a and 3c show an endoscopic needle 12 accessing the wall 82 of the patient lumen 80 through the tissue access port 60 of the end cap 40. As shown in FIGS. 1 and 2, the tissue access port 60 is an aperture formed by removing a portion of the cylindrical end cap's sidewall. The access port 60 may have any length and width, so long as the port 60 does not compromise the structural integrity of the end cap 40. That is, the port 60 cannot be so large as to allow the end cap 40 to collapse during use. In any case, the port 60 has an adequate length and width to allow a medical instrument to access and manipulate patient tissue. Referring to FIGS. 3a–3c, it will be noted that while the tissue port 60 provides access to a tissue site of interest, the rest of the end cap 40 constrains the surrounding tissue. In this regard, the internal chamber 50 provides a working space directly above the tissue site of interest, allowing an endoscopic instrument 100 to more easily perform a medical procedure on a tissue area within a patient lumen.

Referring now to FIGS. 5a–5c, an endoscopic device 100 is illustrated with a suturing apparatus 10 positioned within a tubular member 102 via insertion through a side port 104. As will be appreciated, the endoscopic device 100 may comprise a control device 106 for externally maneuvering the distal end 108 of the endoscopic device 100 so as to facilitate selective access a tissue site of interest within a patient body.

In this regard, the endoscopic device 100 may comprise a number of channels passing therethrough with separate ports at the distal end 108. By way of example, and referring now to FIG. 5b, separate ports 110a, 110b and 110c and 110e may be provided for the positioning of an imaging device, light sources, and an irrigation or suction device therewithin, respectively. Port 110d may be provided for the selective passage of an instrument, such as the suturing apparatus 10 therethrough. When the suturing apparatus 10 is positioned through endoscopic device 100 for access to a tissue site, the suturing apparatus 10 can be advanced/retracted within a field of view of an imaging device that may be located at the distal end 108. In this regard, FIG. 5c illustrates how the suturing apparatus 10 may be viewed when utilized with an endoscopic apparatus 100 having an imaging device 112 interconnected with a real-time user display 200. As illustrated in FIG. 5c, the suturing device contains a piercing tip 14 and needle assembly 12 that project into a field of view defined by the imaging device positioned at the distal end 108 of the endoscopic device 100 so that suturing maneuvers may be readily observed/controlled.

Figure 6A:
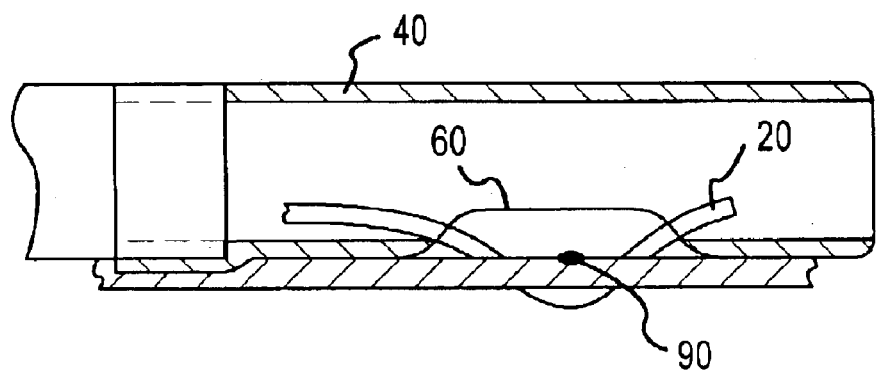
FIGS. 6a–6c show cross-sectional views and an end view of a procedure performed on patient tissue utilizing the present invention.
Figure 6B:
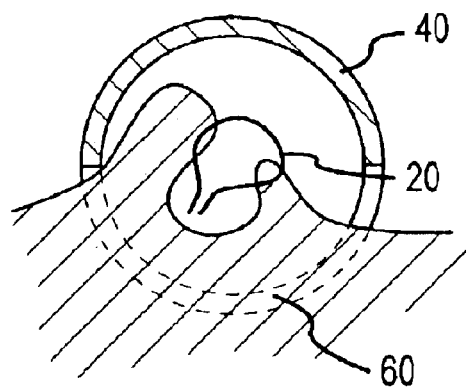
Figure 6C:
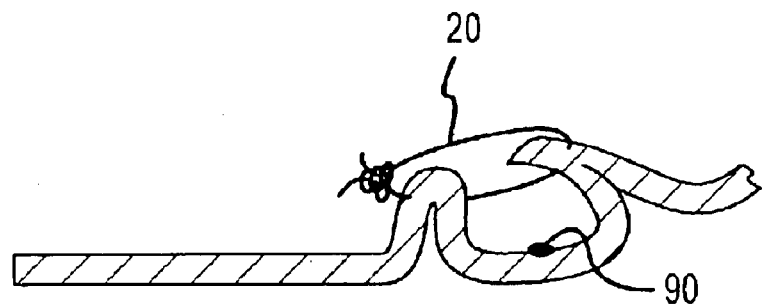

FIGS. 6a–6c in conjunction with FIGS. 3a–3c illustrate utilizing the end cap 40 of the present invention to perform a suturing procedure within a patient lumen 80. In particular, a suturing procedure to close an internal point of interest 90, such as may be caused by removing a polyp within a patient lumen is shown. Initially, the endoscopic device 100 is manipulated until a point of interest 90 is located within the field of view of an optical device such as shown in FIG. 5c. Once located, the tissue port 60 is aligned to provide medical instrument access to the point of interest 90. As shown in FIG. 3a, a suturing apparatus has been advanced through the endoscopic device 100 so that the piercing tip 14 of the needle assembly 12 projects into the internal chamber 50 of the end cap 40. The piercing tip 14 is then extended through the tissue access port 60 to engage the patient tissue. As will be appreciated, remote manipulation of the suture device 10 allows the needle assembly 12 to be oriented such that the piercing tip 14 is able to pass through the patient access port 60 and contact the tissue at the site of interest 90. Suturing may be performed relative to the site of interest 90 utilizing an endoscopic suturing apparatus and method, such as the apparatus and method described in co-pending U.S. patent application Ser. No. 09/662,936, entitled: "Improved Suturing Apparatus and Method", filed on Sep. 15, 2000, the contents of which are incorporated by reference herein as if set forth herein in full.

Upon the piercing tip 14 engaging the tissue at a desired location as shown in FIG. 3a, the suture device 10 is manipulated to rotate the piercing tip 14 to an upward position. Thereafter, as shown in FIG. 3b, the suture device 10 advances the piercing tip 14 a desired distance forward such that the piercing tip 14 passes back through the patient tissue. As shown in FIG. 3b, the end cap 40 facilitates the suturing procedure by providing a working space for instrument manipulation relative to the site of interest. Additionally, the forward edge or lip 62 of the tissue access port 60 is utilized as a needle backstop that provides a convenient means for passing the needle 12 through the flaccid tissue. That is, without the lip 62, it may be difficult to pass the needle 12 through the soft, pliable tissue. By pressing the engaged tissue against lip 62 and advancing the needle 12, the tissue may be more easily pierced/sutured.

As shown in FIG. 6a, the needle 12 may be utilized to dispose a suture 20 through the patient tissue relative to a point of interest 90. In a known manner, the suture material may be grasped and released by the needle 12 to form a second suture on one or more sides of the point of interest 90. As shown in FIGS. 6b and 6c, once a number of sutures are placed around the point of interest 90, the suture material 20 may be cinched to close the point of interest 90. That is, through repeated manipulations of the endoscopic device 100 and needle assembly 12, suture material 20 may be utilized to close the point of interest 90. As will be appreciated, the hollow internal chamber 50 provided by the flexible end cap 40 provides a working space above the point of interest 90 that allows for medical instruments such as the needle assembly 12 to be lifted, rotated, advanced, extracted, and otherwise manipulated relative to the point of interest 90 free of interference from surrounding tissue.

FIGS. 4a and 4b illustrate an alternate embodiment of the end cap 40 that contains a closed distal end 42 to perform a suturing procedure. In this embodiment, one of the ports 110a–c of the endoscopic device selectively provides suction that, as shown in FIG. 4a, pulls a portion of the tissue 80 into the tissue access port 60. Once disposed through the port 60, the tissue 80 is pierced by a straight needle 16. That is, the needle 16 is able to advance linearly to press the tissue 80 against the backstop 62. As will be appreciated, utilizing the closed end cap 40, suction, and a straight needle 16 allows enhanced control of needle depth penetration into the tissue 80. That is, the needle is restricted from penetrating too deeply into the patient tissue that may result in perforation through an opposing wall 82 of the tissue lumen 80.

The embodiments described above are for exemplary purposes only and is not intended to limit the scope of the present invention. Various adaptations, modifications and extensions of the embodiment will be apparent to those skilled in the art and are intended to be within the scope of the invention as defined by the claims that follow.

What is claimed:

1. An endoscopic device including a tube member having a distal end adapted for insertion into a patient and an imaging apparatus for providing an image of an area proximate to said distal end of said tube member, said endoscopic device further comprising:
    a housing for selective attachment to a distal end of an endoscopic device, said housing having an internal chamber;
    a first aperture extending through said housing to said internal chamber, said first aperture being adapted to engage said distal end of said tube member;
    a second aperture extending through said housing to said internal chamber for providing access to patient tissue disposed adjacent to said housing during an endoscopic procedure; and
    a needle selectively moveable from a first position within said internal chamber through said second aperture to a second position outside of said internal chamber, wherein in said second position said needle projects from said housing and is engageable with patient tissue, and wherein said needle is moveable from said second position to said first position to dispose engaged tissue through said second aperture into said internal chamber.

2. The endoscopic device as recited in claim 1, wherein a portion of said needle that projects from said housing in said second position is at least generally arcuate.

3. The endoscopic device as recited in claim 2, wherein said needle is rotateable from a first angular position to a second angular position.

4. The endoscopic device as recited in claim 1, wherein said first aperture extends through a first end of said housing and said second aperture extends through a sidewall of said housing.

5. The endoscopic device as recited in claim 4, further comprising a third aperture extending through said housing.

6. The endoscopic device as recited in claim 5, wherein said third aperture extends through a second end of said housing substantially opposite of said first end.

7. The endoscopic device as recited in claim 1, wherein said first aperture is sized to slidably receive a distal end of an endoscopic device.

8. The endoscopic device as recited in claim 7, wherein said first aperture is adaptable to receive a distal end of a plurality of differently sized tube members.

9. The endoscopic device as recited in claim 1, wherein said housing is substantially tubular.

10. The endoscopic device as recited in claim 9, wherein said housing has a diameter between about 4 mm and 28 mm.

11. The endoscopic device as recited in claim 1, wherein said housing is an elongated member.

12. The endoscopic device as recited in claim 11, wherein said elongated member has a length between about 15 mm and 76 mm.

13. The endoscopic device as recited in claim 1, wherein said second aperture has a length between about 4 mm and 37 mm and an angular width between about 45° and about 270°.

14. The endoscopic device as recited in claim 1, wherein said housing comprises a substantially transparent material.

15. The endoscopic device as recited in claim 1, wherein said housing comprises a semi-rigid polymeric material.

16. The endoscopic device as recited in claim 1, wherein said first needle is selectively moveable from a lumen within said tube member to said first position within said internal chamber.

17. The endoscopic device as recited in claim 16, wherein said imaging apparatus is operative to provide an image of said internal chamber.

18. An endoscopic device, comprising:
  a tube member having a distal end adapted for insertion into a patient body;
  a housing having an internal chamber, said housing being interconnected to said distal end of said tube member wherein said tube member extends through a first aperture in said housing and a second aperture extends through a sidewall of said housing;
  an imaging apparatus positionable relative to said distal end, said imaging apparatus being operative to provide a field of view of said internal chamber; and
  a needle having an arcuate distal end, said needle being positionable through said distal end of said tube member, wherein said needle is advanceable through said second aperture to engage patient tissue and retractable through said second aperture to dispose engaged tissue into said internal chamber and into said field of view.

19. The endoscopic device as claimed in claim 18, wherein said tube member includes a plurality of lumens, wherein said needle is disposed in one of said plurality of lumens.

20. The endoscopic device as claimed in claim 19, wherein at least one additional endoscopic instrument is positionable through another one of said plurality of lumens.

21. The endoscopic device as claimed in claim 20, wherein said at least one endoscopic instrument is selectively advanceable into said internal chamber.

22. The endoscopic device as claimed in claim 20, wherein said at least one endoscopic instrument is further advanceable through said second aperture.

23. The endoscopic device as claimed in claim 20, wherein said endoscopic instrument is selected from a group consisting of:
  a light source; and
  a medical device.

24. The endoscopic device as claimed in claim 23, wherein said medical device comprises at least one of:
  a scalpel;
  a laser device;
  an electrosurgical tip; and
  a gas beam fulgerator.

25. The endoscopic device as claimed in claim 18, wherein said needle further comprises suture material.

26. The endoscopic device as claimed in claim 18, wherein said tube member includes a vacuum lumen for selectively applying a vacuum to said internal chamber of said housing.

27. The endoscopic device as claimed in claim 18, further comprising:
  a display device interconnected to said endoscopic device for displaying an image to a user on a real-time basis.

28. A method for performing an endoscopic procedure, said method comprising:
  first positioning an endoscopic capsule disposed on the end of a tube member adapted for insertion into a patient body relative to a target area of patient tissue within a patient lumen, said capsule having an internal chamber;
  second positioning an aperture extending through said capsule to said internal chamber adjacent to said target area of patient tissue;
  first advancing a suture device associated with an endoscopic device from a first position within said tube member into said internal chamber;
  disposing at least a portion of said target area of patient tissue through said aperture into said internal chamber;
  suturing said target area of patient tissue, wherein said suturing is performed within said internal chamber.

29. The method as recited in claim 28 wherein said step of positioning said capsule dilates a patient tissue lumen.

30. The method as recited in claim 28, further comprising:
  interconnecting said endoscopic capsule to the end of said tube member, wherein said step of interconnecting is performed at a medical care facility.

31. The method as recited in claim 28, further comprising:
  interconnecting said endoscopic capsule to the end of said tube member, wherein said step of interconnecting is performed by a endoscopic device manufacturer.

32. The method as recited in claim 28, wherein said step of second positioning further comprises externally manipulating said tube member to align said aperture with said target area of patient tissue.

33. The method as recited in claim 28 wherein said step of disposing includes engaging said target area of patient tissue via said aperture.

34. The method of claim 33, wherein said step of engaging comprises second advancing said suture device disposed within said internal chamber at least partially through said aperture to engage said target area of patient tissue.

35. The method as recited in claim 28, wherein said step of first advancing a suture device comprises advancing a needle through said aperture.

36. The method as recited in claim 35, wherein said suturing step further comprises:
  utilizing said needle to pierce said target area of patient tissue; and disposing suture material through said target area of patient tissue.

37. The method as recited in claim 28, wherein said step of disposing comprises pulling said target area of patient tissue into said internal chamber.

38. The method as recited in claim 37, wherein said step of pulling comprises utilizing a suction force pull said tissue into said chamber.

39. The method as recited in claim 28, further comprising: illuminating at least a portion of said internal chamber of said capsule.

40. The method as recited in claim 28, further comprising: imaging at least a portion of said internal chamber of said capsule, wherein an interconnected display device displays an image to a user on a real-time basis.

41. A method for performing an endoscopic procedure, said method comprising:
   positioning an endoscopic capsule disposed on the end of a tube member adapted for insertion into a patient body relative to a target area of patient tissue within a patient body, said capsule having an internal chamber;
   applying suction through said tube member and said capsule to dispose said target area of tissue through an aperture extending through said capsule to said internal chamber;
   restricting movement of at least a portion of said target area of tissue relative to said aperture; and
   advancing a needle through at least a portion of said target area of tissue disposed within said internal chamber, wherein said needle advances form a first position within said internal chamber to a second position within said internal chamber in conjunction with said advancing.

42. The method as claimed in claim 41, wherein said positioning step further comprises positioning said aperture adjacent to said target area of tissue.

43. The method as claimed in claim 41, wherein said disposing step further comprises:
   advancing a distal end of said needle through said aperture to engage a portion of said target area of tissue; and
   utilizing said needle engaged with said portion of tissue to pull said tissue back through said aperture to complete said disposing step.

44. The method as claimed in claim 41, wherein said restricting step comprises contacting said target area of tissue with a rim portion of said aperture.

45. The method as claimed in claim 44, wherein said restricting step comprises compressing said target area of tissue between said rim portion of said aperture and a distal end of said needle.

46. The method as claimed in claim 41, wherein said inserting step further comprises:
   disposing suture material associated with said needle through said portion of said target area of tissue.

47. The method as claimed in claim 46, further comprising:
   withdrawing said needle from said target area of tissue, wherein said suture material remains disposed through said target area of tissue.

* * * * *